(12) United States Patent
Lo et al.

(10) Patent No.: US 6,843,771 B2
(45) Date of Patent: Jan. 18, 2005

(54) ULTRASONIC MONITOR FOR MEASURING HEART RATE AND BLOOD FLOW RATE

(75) Inventors: Thomas Ying-Ching Lo, Fremont, CA (US); Tolentino Escorcio, Dublin, CA (US)

(73) Assignee: Salutron, Inc., Fremont, CA (US)

( * ) Notice: Subject to any disclaimer, the term of this patent is extended or adjusted under 35 U.S.C. 154(b) by 0 days.

(21) Appl. No.: 10/346,296

(22) Filed: Jan. 15, 2003

(65) Prior Publication Data

US 2004/0138568 A1 Jul. 15, 2004

(51) Int. Cl.⁷ .................................................. A61B 8/14
(52) U.S. Cl. ..................................... 600/459; 600/465
(58) Field of Search ............................. 600/437–472, 600/500, 503; 128/916, 846; 73/625, 626; 601/2, 3

(56) References Cited

U.S. PATENT DOCUMENTS

| | | | |
|---|---|---|---|
| 4,086,916 A | | 5/1978 | Freeman et al. |
| 4,163,447 A | | 8/1979 | Orr |
| 4,256,117 A | | 3/1981 | Perica et al. |
| 4,556,066 A | | 12/1985 | Semrow |
| 5,197,489 A | | 3/1993 | Conlan |
| 5,243,992 A | | 9/1993 | Eckerle et al. |
| 5,431,170 A | | 7/1995 | Mathews |
| 5,474,072 A | * | 12/1995 | Shmulewitz ............... 600/446 |
| 5,494,038 A | * | 2/1996 | Wang et al. ............... 600/459 |
| 5,795,300 A | | 8/1998 | Bryars |
| 5,807,267 A | | 9/1998 | Bryars et al. |
| 5,810,736 A | | 9/1998 | Pail |
| 6,080,111 A | | 6/2000 | Pao-Lang |
| 6,394,960 B1 | | 5/2002 | Shinogi et al. |
| 6,447,456 B1 | | 9/2002 | Tsubata |
| 6,554,772 B2 | | 4/2003 | Nakamura et al. |
| 6,584,660 B1 | | 7/2003 | Shimogawa et al. |
| 6,716,169 B2 | | 4/2004 | Muramatsu et al. |
| 6,744,178 B2 | | 6/2004 | Muramatsu et al. |
| 6,758,816 B1 | | 7/2004 | Tsubata et al. |
| 6,767,329 B2 | | 7/2004 | Amano et al. |
| 2001/0034486 A1 | | 10/2001 | Larson et al. |
| 2001/0056243 A1 | | 12/2001 | Ohsaki et al. |
| 2002/0151810 A1 | | 10/2002 | Wong et al. |

OTHER PUBLICATIONS

Dow Corning Product Description.
Teknor Apex Product Description.
GLS Corporation Product Description.
Septon Product Description.
Kraton Product Description.
Gelest Product Description.

\* cited by examiner

*Primary Examiner*—Ali Imam
(74) *Attorney, Agent, or Firm*—Vierra Magen Marcus; Harmon & DeNiro LLP

(57) ABSTRACT

The invention provides an ultrasonic monitor for measuring pulse rate values in a living subject, including a module with at least one source of ultrasonic energy, a gel pad comprised of a polymer and from about 50 to about 95% by weight of an ultrasound conductive diluent, wherein the gel pad is positioned in direct contact between the module and the living subject; an ultrasonic energy detector and associated hardware and software for detecting, calculating and displaying a readout of the measured rate values.

17 Claims, 4 Drawing Sheets

ULTRASONIC MONITOR FOR MEASURING HEART RATE AND BLOOD FLOW RATE

BACKGROUND OF THE INVENTION a) Field of the Invention

The present invention relates to ultrasonic monitors for measuring heart and pulse rates in living subjects. Methods for measuring heart and pulse rates of living subjects through ultrasonic means are also encompassed by the instant invention.

b) Description of Related Art

Measuring Heart and Pulse Rates

Measuring heart and pulse rates in living subjects has been accomplished by various means. The pulse rate is commonly measured by lightly touching one's fingers over an artery and counting the rate of pulsation. The heart rate is usually measured by a sensing device using electrodes that monitor the electrical activity of the heart (e.g., contact monitors) based on electrocardiograms (EKG OR ECG). Measuring rate values is a useful tool in individualizing and optimizing exercise regimens. Individuals who want to increase endurance or performance aim for certain target heart rates to maximize progression towards their goals. Conversely, adults with a history of heart disease must avoid exceeding a certain heart or pulse rate to reduce unnecessary strain on the heart and resultant injury.

The heart rate is the rate of contractions over a given time period, usually defined in beats per minute. A pulse can be defined as the rhythmical dilation of a vessel produced by the increased volume of blood forced into the vessel by the contraction of the heart. The pulse can be felt at many different points on the body, including the wrist (radial artery) and neck (carotid artery), which are among the most easily accessible points. Since a heart contraction almost always produces a volume of blood that can be measured as a pulse, the heart rate and pulse rate are usually the same. However, there are certain situations where the pulse rate may differ from the heart rate. For example, the body may generate an irregular heart beat or a premature heart beat. In this scenario, a heart contraction would not force out enough blood to be measured as a pulse and the measured pulse rate would be different from the heart rate.

Heart rate monitors that provide continuous heart rate readings rather than a single point measurement require wearing a chest strap. There are a few heart rate monitors that do not require a chest strap. Most, if not all, of these monitors do not provide continuous heart rate readings but measure the wearer's pulse and transmit that pulse upon request. Most users would have to stop exercising in order to get this type of measurement, which is disruptive to an exercise regimen. In U.S. Pat. Nos. 5,738,104 and 5,876,350 and European Patent No. 0861045B1, Lo et al disclosed an EKG heart rate monitor that does not require a chest strap so that the user does not have to stop exercising to take a heart rate measurement. All the sensors and electronics are contained in a wristwatch. The software is effective in filtering out muscle motion noise. Therefore the user can walk and jog while taking a single point measurement. However, this technology still does not offer continuous readings. Hence, most users or heart patients that demand continuous heart rate readings choose a monitor that requires a chest strap. Most of the population, including the elderly, would prefer a monitor that does not require a chest strap. There are also portable patient monitors (e.g., vital signs monitors, fetal monitors) that can perform functions as diverse as arrhythmia analysis, drug dose calculation ECG waveforms cascades, and others. However, such monitors are usually fairly large (e.g., size of a small TV) and are connected to the patient through specific wires. The art has, thus, a need for an improved heart monitoring device, specifically one that provides continuous heart rate readings for both healthy and compromised living subjects without the need for chest straps, wirings, or the like.

It is well known in the prior art to employ sonar technology to identify moving objects. A piezoelectric crystal may be used both as the power generator and the signal detector. In this case, the ultrasonic energy is emitted in a pulsed mode. The reflected signal is picked up by the same crystal after the output power source is turned off. The time required to receive the reflected signal depends upon the distance between the source and the object. The frequency shift, better known as Doppler shift, is dependent upon the speed of the moving object. This technique requires only one crystal but the detector circuit will only work after the transmitter power is turned off. It is conceivable to use this method to detect the motion of a blood vessel wall to extract the pulse rate information. However, for superficial blood vessels this technique requires very high speed power switching due to the short distance between source and object. In addition, muscle movement will also generate reflections that compromise the signal-to-noise-ratio in the system. The muscle noise signal in this case is very similar to the signal due to blood vessel wall motion. Therefore, it is very difficult to detect heart rate this way when the living subject is in motion. The advantage of this approach, however, is low cost and low power consumption. For continuous mode two piezoelectric elements may be used. Either may be used as the transmitter and the other as receiver or detector at a given time. These two elements can be positioned at an angle to the direction of the flow on opposite sides or on the same side of the conduit. If they are on the same side, the two crystals can be conveniently packaged into a module. The flow rate or flow velocity is proportional to the Doppler shift relative to the operating frequency. The main advantage of continuous mode for pulse rate application is that the Doppler shift due to blood flow is distinctly different from the shifts due to muscle artifacts or tissue movement. The shift due to blood flow is higher in frequency than that due to muscle motion. Therefore, even if the muscle motion induced signals are larger in amplitude, they may still be filtered out by a high pass filter in either analog or digital form to retain the blood flow signals. In this respect the ultrasound method is superior to infrared, pressure sensing and even EKG based technologies.

One device useful for the measurement of heart and pulse rates is an electronic unit worn on the wrist. Several such devices are known in the art. U.S. Pat. No. 4,086,916 (Freeman et al.) discloses a cardiac wristwatch monitor having ultrasonic transducers mounted in the wrist strap portion. The transducers are encased in an epoxy and covered with an insulative coating. U.S. Pat. No. 4,163,447 (Orr) discloses a wrist-mounted heartbeat rate monitor that relies upon light-emitting diodes. U.S. Pat. No. 4,256,117 (Perica et al.) discloses a wrist-mounted combination stopwatch and cardiac monitor that uses a pressure transducer to measure pulse rate.

In Freeman's invention, a wristwatch was intended to offer a continuous pulse rate monitor. However, ultrasonic energy is prone to diffraction and attenuation at the interface of two media of different densities. Any air gap at the interface or any air bubbles in the media will also make ultrasonic energy transfer unreliable. Therefore, it has been a standard practice to apply water or an aqueous gel between the transducer module and the living subject to eliminate any air gap. Unfortunately water and aqueous gels dry up quickly in open air. For continuous rate monitoring, the requirement to apply water or gel frequently is not acceptable. In U.S. Pat. Nos. 6,371,920 B1 and 6,394,960 B1 attempts were made to overcome this problem by using an array of small transducers protruding from the support surface to make firm contact with a living subject with no air gap in between. However, this increases the complexity and cost of the transducer device and its driving electronics significantly. The air gap will not be totally removed, either, due to body hairs and the variable condition of skin from person to person. In U.S. Pat. No. 6,447,456 B1, two sets of transducers are used at the radial artery and the ulnar artery. The idea is to cope with the compromised signal quality due to motion at the wrist that may create an air gap from time to time. With two sets of transducers the hope is that at least one of them will reliably detect the Doppler signal to identify the heart beat. The disadvantages of continuous mode over pulsed mode are higher cost and more power consumption.

SUMMARY OF THE INVENTION

The present invention relates to an ultrasonic monitor for measuring rate values of a living subject, including heart rate and pulse rate. Due to continued advances in piezoelectric material and microelectronic technologies, an ultrasound based pulse rate monitor system can be miniaturized to reduce cost and power consumption.

One aspect of the invention provides an ultrasonic monitor for measuring pulse rate values in a living subject, including a module with at least one source of ultrasonic energy, a gel pad comprised of a polymer and from about 50 to about 95% by weight of an ultrasound conductive diluent, wherein the gel pad is positioned in direct contact between the module and the living subject; an ultrasonic energy detector and associated hardware and software for detecting, calculating and displaying a readout of the measured rate values. The gel pad is made of a polymer having the following characteristics:

a) Hardness: Needle Penetration from about 5 to about 300 (1/10 mm) according to ASTM D15, preferably from about 25 to about 150, and most preferably from about 30 to about 50;

b) Tensile Strength from about 5 to about 500 psi according to ASTM D412, preferably from about 10 to about 300 psi, and most preferably from about 50 to about 200 psi; and c) Elongation from about 50% to about 800% according to ASTM D412, preferably from about 200% to about 700%, and most preferably from about 300% to about 500%.

The gels are stable after stress and temperature cycling (with no oil exuding out). The display may optionally include electronics and software for analyzing the rate values from a living subject. Conversely, the module may include the electronics and software for analysis of the rate values.

Another aspect of the invention provides a method of measuring rate values of a living subject. The method includes providing an ultrasonic monitor as described above and contacting the monitor with the living subject.

BRIEF DESCRIPTION OF THE DRAWINGS

The present invention is best understood when read in conjunction with the accompanying figures which serve to illustrate the preferred embodiments. It is understood, however, that the invention is not limited to the specific embodiments disclosed in the figures.

DETAILED DESCRIPTION OF THE INVENTION a) Definitions and General Parameters

The following definitions are set forth to illustrate and define the meaning and scope of the various terms used to describe the invention herein.

The terms "ultrasonic" and "ultrasound" are used interchangeably herein and refer to a sound wave having a frequency between about 1 MHz and about 10 MHz. An "ultrasonic transducer" (i.e., a transducing means) is a device used to introduce sonic energy into a test object (e.g., living subject) and also to detect reflected energy from the object as in the instant invention. Typical of this type of device are piezoelectric crystals which respond to electric pulses from an instrument with a mechanical pulse, and to mechanical pulses (reflected energy) from the test object with electrical energy detectable by the instrument. Ultrasound may also be used as a sound wave imaging technique used to examine a part of the body (e.g., breast, abdomen, heart) in order to evaluate a specific tissue or progression of a diseased tissue. In addition, ultrasound is used to monitor fetuses and their growth.

A "rate value" as used herein, refers to a value that can be measured. A rate value of the instant invention includes, but is not limited to, a heart rate, pulse rate, fetal heart rate, and fetal pulse rate.

Figure 1:
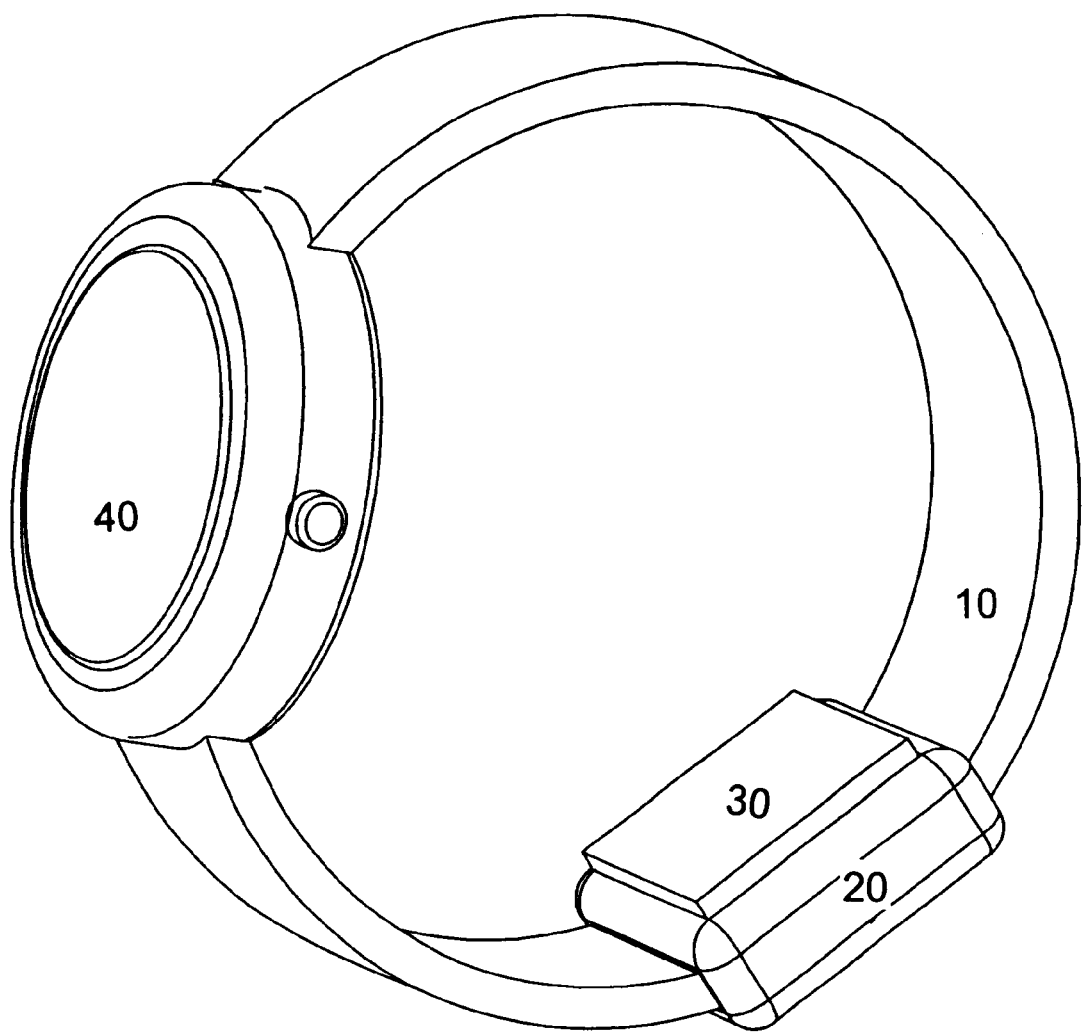
FIG. 1 depicts a front view of an ultrasonic monitor of the instant invention. Shown here is a wristwatch with attached wristband (10) having a module (20) with a gel pad (30), wherein the gel pad contacts the skin of a living subject. The figure also depicts the display unit (40) which provides a readout of measured rate values.
Figure 2:
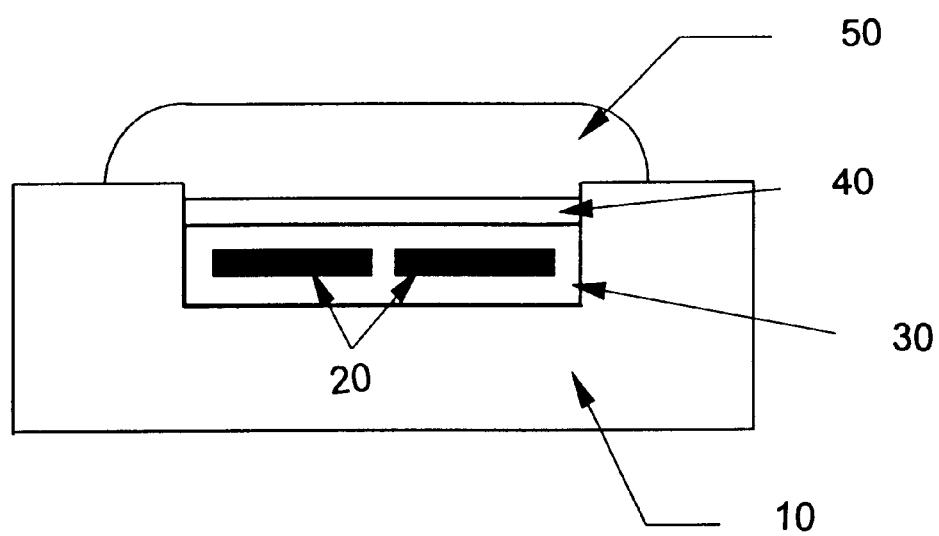
FIG. 2 depicts a cross sectional view of a transducer module assembly. The substrate of the housing (10) may be metal or plastic. The transducers (20) are molded in ABS and permanently adhered to the housing. On top of the transducer module (30), there is an optional thin adhesive layer (40) which can be a lower oil content gel or an appropriate adhesive material. The top structure is the gel pad (50) that is in direct contact with the living subject.
Figure 3:
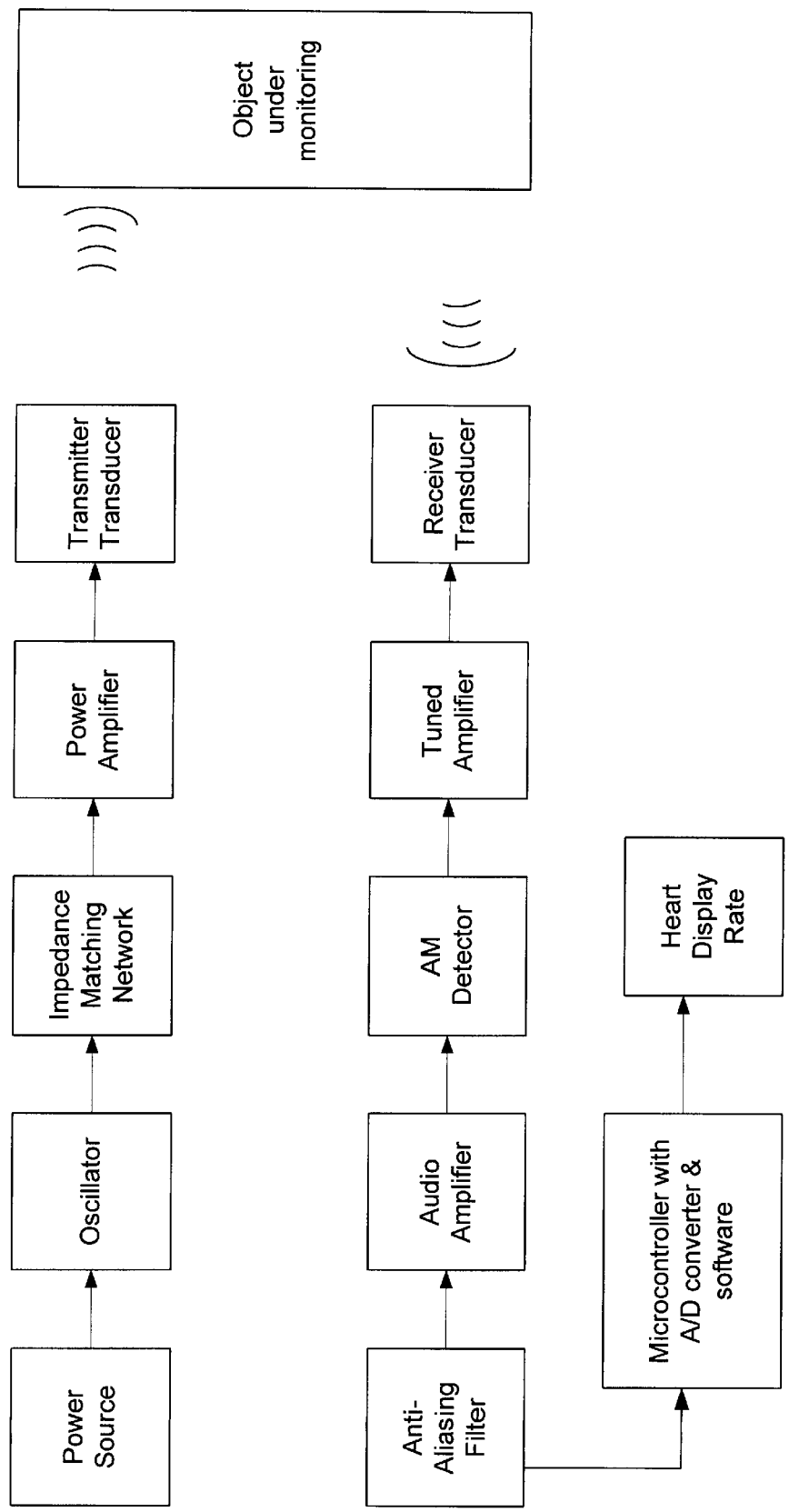
FIG. 3 depicts a block diagram of a typical ultrasound based heart rate monitor system.
Figure 4:
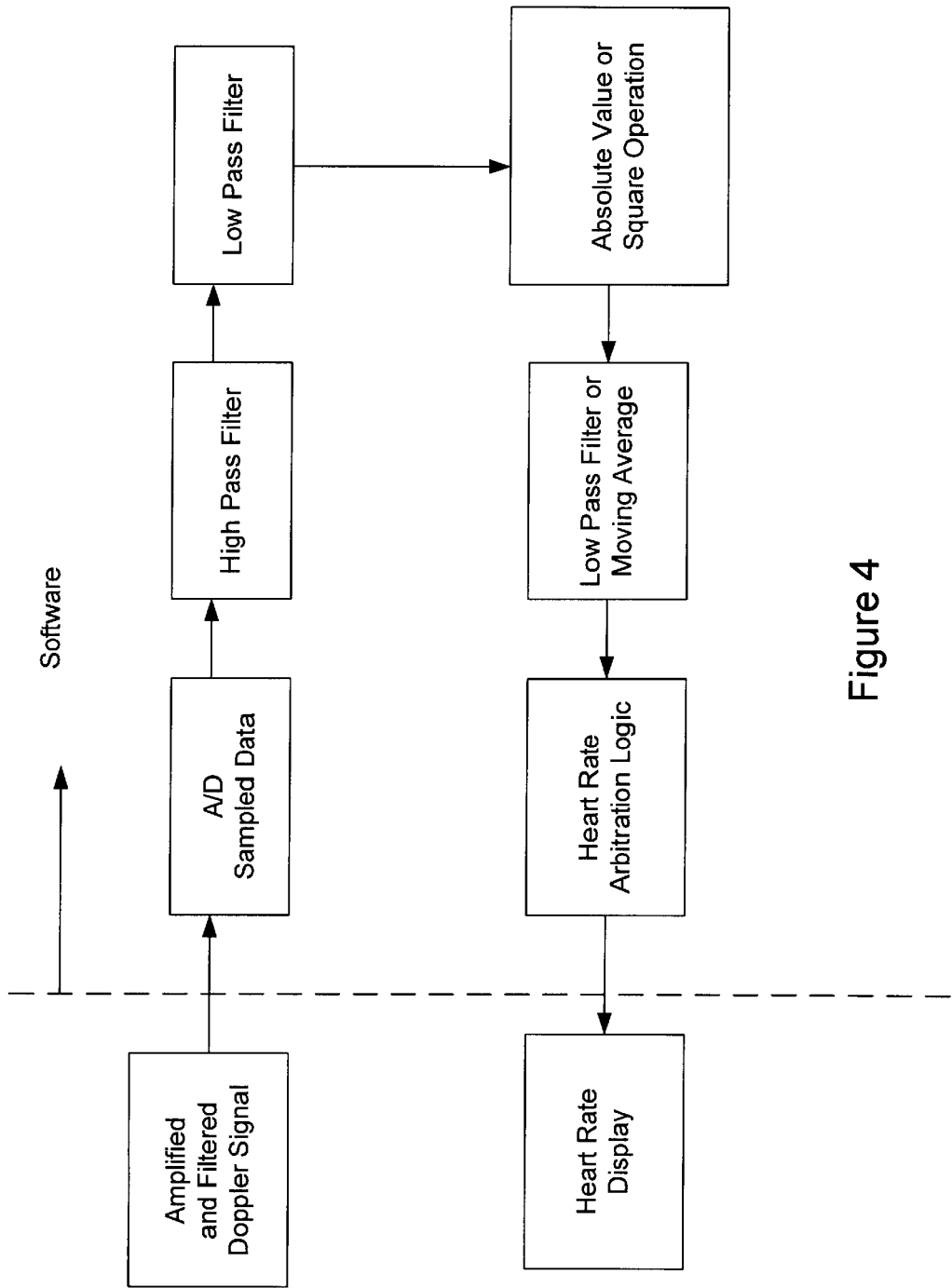
FIG. 4 depicts the block diagram of the software of this invention. The amplified Doppler signal after anti-aliasing filtering is sampled by an A/D converter in a microcontroller. The sampled data is further digitally filtered by a high pass filter or a combination of high pass and low pass filters. The output is applied with either an absolute value operator or a square operator followed by a stage of low pass filter. Finally this digitally processed data is used to determine the pulse rate.

The term "module with transducing means" refers to the assembly that contains the piezoelectric transducer. See, for example, FIG. 2. The module may optionally include electronics for analysis of the rate values.

The term "thermoset gel" as used herein refers to a gel that is generally made of a chemically bonded three-dimensional elastomeric network which entraps a large amount of low volatility liquids or diluents. The elastomeric network is permanent and cannot be reversed to a liquid state through heating. A certain amount of diluent is necessary in order to ensure good conformability of the gel to the skin and low attenuation for ultrasound transmission while still maintaining the load bearing properties. The gel can be used at a temperature that ranges from −30° C. to +70° C., wherein the gel maintains its shape and load-bearing elastic properties. A "silicone gel" or a "polyurethane gel" is an example of a thermoset gel. Prior to this invention, thermoset gels have not been used as ultrasound transmission media.

The term "thermoplastic gel" as used herein refers to a gel that is generally made of a thermoplastic elastomer with a large proportion of interdispersed diluent. Thermoplastic elastomers include block copolymers such as styrene-butadiene-styrene, styrene-isoprene-styrene, styrene/ethylene-co-butylenes/styrene, and styrene/ethylene-co-propylene/styrene. The styrene end blocks form glassy domains at room temperature. The glassy domains act as physical crosslinks that provide the elastomeric properties of the polymer. During heating above the glass transition temperature of styrene, i.e., about 100° C., the glassy domains melt and the polymers revert to a liquid state. During cooling, the glassy domains re-form again. Hence, the process is reversible. Other block copolymers, such as ethylene-(ethylene-co-butylene)-ethylene copolymers which contains crystalline polyethylene end blocks, can also be used to prepare thermoplastic gels. Prior to this invention, thermoplastic gels have not been used as ultrasound transmission media.

b) The Ultrasonic Monitor

One aspect of the invention provides an ultrasonic monitor for measuring pulse rate values in a living subject, including a module with at least one source of ultrasonic energy (transducer), a gel pad comprised of a polymer and a mineral oil, wherein the gel pad is positioned in direct contact between the module and the living subject; an ultrasonic energy detector and associated hardware and software for detecting, calculating and displaying a readout of the measured rate values. The gel pad is made of a polymer having the following characteristics:

a) Hardness: Needle Penetration from about 5 to about 300 (1/10 mm) according to ASTM D15, preferably from about 25 to about 150, and most preferably from about 30 to about 50;

b) Tensile Strength from about 5 to about 500 psi according to ASTM D412, preferably from about 10 to about 300 psi, and most preferably from about 50 to about 200 psi; and c) Elongation from about 50% to about 800% according to ASTM D412, preferably from about 200% to about 700%, and most preferably from about 300% to about 500%.

In a preferred embodiment of the invention, the monitor is a wristwatch with attached wristband, wherein the module is attached to the wristband. In another preferred embodiment the transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the module includes a pair of piezoelectric crystals at an angle to each other, wherein the angle is determined by the depth of the object being monitored. If the object is a fetus deep inside a womb, the two crystals are placed parallel to each other. If the object is the radial artery of a human subject (e.g., adult, infant), the angle of the two crystals with respect to the direction of the blood flow would be about 5 to about 20 degrees. One of the crystals is energized at an ultrasonic frequency. The signal is then reflected back by the living subject and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow.

The ultrasonic monitor includes an ultrasonic frequency driver, an AM or FM detector, an amplifier, filter circuits and a microcontroller. The driver circuit is composed of an oscillator running at a frequency between about 1 MHz to about 10 MHz, an impedance matching network and a Class C power amplifier. Ultrasonic energy is delivered to one of the two piezoelectric elements in the module by the power amplifier. The other element picks up the reflected ultrasonic signal. This signal is amplified and then amplitude demodulated(AM) or frequency demodulated(FM) to yield the Doppler frequencies. The Doppler frequencies in audio range are further amplified and filtered to avoid aliasing before they are digitally sampled and processed by a microcontroller with built-in analog-to-digital converter and software. The software digitally filters out the noise signals due to muscle artifacts by a high pass filter with a 3-db corner frequency at about 100 to about 1500 Hz depending on the original ultrasound operating frequency. Following that, a square operation and a low pass filter will further condition the signal appropriately for heart rate arbitration. The 3-db corner frequency of the low pass filter is about 1000 to about 5000 Hz depending upon the original ultrasound operating frequency. The heart rate arbitration logic in the prior art of Lo et al. may be applied to this invention with minor modifications.

The module may optionally include electronics and software for analyzing the rate values of the living subject, such as heart rate or pulse rate. Alternatively, the display unit may include the electronics and software for analyzing the rate values. As such, there are at least two alternative embodiments with respect to the wrist watch ultrasonic monitor. In one embodiment of the invention, the transducers, the electronics and the software are all housed in the same module. The module is mechanically attached to the wrist band and it may be positioned at the radial artery of a living subject. The gel pad faces the wrist of the living subject and is held in place by the wrist band. The two crystals (supra) are located in the interior of the module right behind the gel pad. The measured blood flow and/or heart rate values can be sent to the watch display unit via wireless means. In this case, the module has a transmitter circuit and the display unit has a receiver circuit. The carrier frequency may be chosen based upon conventionally used frequencies, e.g. 5 KHz, 120 KHz, 455 KHz, 433 MHz, 900 MHz, etc. These frequencies are used in various chest strap heart rate monitors. Currently, the most popular frequency used is 5 KHz. Therefore, the module with all the electronics and software included may be offered as a direct replacement to the existing chest strap products in the market. The display unit in this case is the wristwatch with wireless receiver circuit built-in. Optionally, the module can be fastened separately on its own strap adapted to fit another part of the living subject where blood flow can be conveniently monitored. This is the preferred approach since the battery compartment in the module may be designed to allow users to replace the battery with ease. The frequency of use and the length of time per use determine how frequently the battery needs to be replaced for a given type of battery.

In another embodiment of the invention, the same electronics and software are placed within the watch display unit while the transducers and gel pad are housed within the module. Connecting wires are molded into the wrist band to connect to the ultrasound driving circuit. In this case, a high energy density battery is required to reduce the frequency of battery change. Alternatively, a rechargeable battery may be employed. The battery will be charged wirelessly so that the watch unit is waterproof for swimmers and divers. As battery technology continues to improve in energy density and lifetime, this integrated approach may eventually be preferred. In another embodiment, the monitor may be held in place by or integrated into a head band for monitoring temporo pulses.

Examples of rate values that can be measured with the ultrasonic monitor include, but are not limited to, heart rate values and blood pulse rate values. Such rate values can be obtained from human adults, infants, and fetuses or from other animals.

c) Polymers and Gels

The ultrasonic monitor includes a gel pad which is positioned in direct contact with the module and the living subject. Ultrasound energy does not propagate efficiently through air, thus a couplant (gel pad) is needed for efficient transmission between the transducer and the living subject. Gels in fluidic state may be used as couplants, however, such fluidic gels are likely to dry up quickly due to being water based. Hence, the instant invention preferably employs oil based gels in solid form to achieve efficient transmission between the transducer and the object. As such, the gel pad is made of a specific polymer which is used to conduct ultrasound waves such that the waves can be converted to measurable rate values. In a preferred embodiment, the polymer is a thermoset or thermoplastic gel. The gel of the present invention may include any elastomer type, elastomer molecular weight, crosslinking density, percentage of diluents, and the like. The gel pad may be about one square centimeter in size and its shape may be square, rectangular or round. Examples of thermoset gels include, but are not limited to, silicone or polyurethane gels. Silicone gels can be based on the reaction between a vinyl terminated polydimethylsiloxane, polymethylphenylsiloxane, or polydiphenylsilocaxane, and a hydride terminated polydimethylsiloxane, polymethylphenylsiloxane, or polydiphenylsiloxane. Polyurethane gels can be based upon the reaction of polybutadienediol, polybutadienetriol, poly(ethylene-co-propylene)diol, poly(tetraethylene oxide)diol, poly(ethylene oxide)diol, or castor oil with polyisocyanates such as toluene diisocyanate, or methylene diisocyanates. Examples of thermoplastic gels include, but are not limited to, styrene-(ethylene-co-butylene)-styrene, styrene-(ethylene-copropylene)-styrene, styrene-butadiene-styrene, styrene-isoprene-styrene ethylene-(ethyleneco-butylene)-ethylene and other elastomeric block copolymers.

The term "gel" is often used to describe a wide variety of materials which may have different properties. The art generally distinguishes three types of gels: thickened fluids, hydrogels, and stable soft elastomeric gels. Examples of thickened fluids are toothpastes, dishwasher detergents, and the like. These fluids are typically thickened by fumed silica, bentonite clay, or other inorganic thickening agents. Upon gentle shaking or squeezing, this type of gel flows readily in a liquid-like fashion. However, this gel cannot recover its original thickened shape. Such gels are, thus, not suitable for applications where the gel needs to take on a specific shape or form.

Hydrogels typically include water soluble, high molecular weight polymers such as poly(vinyl alcohol), polyacrylamide, poly(acrylic acid), and the like. Hydrogels also contain a high percentage of water or water compatible fluids such as glycol. Hence, hydrogels can be characterized as water-like fluids or water compatible fluids, thickened by a high molecular weight organic polymer. Furthermore, this type of gel, depending on the composition, can be a fluid or elastic solid. If a lower molecular weight water soluble polymer and/or a high percentage of water is used, a fluid-like hydrogel is formed. A fluid-like hydrogel such as AQUASONIC™ hydrogel is widely used as a medium for ultrasonic transmission. In fact, there are several commercial gel products used for ultrasonic transmission, often simply referred to as ultrasound gel or ultrasound transmission gel. U.S. Pat. Nos. 6,328,695; 6,251,076; and 6,159,149 refer to the use of a gel as transmission medium with respect to their patented ultrasonic devices. If a high molecular weight water soluble polymer and/or a low percentage of water is used, the gel can form a soft elastic solid which is capable of carrying a moderate level of mechanical stress. The elasticity is derived from the temporary network formed by hydrogen bonding of water molecules to the polar groups of the polymers. U.S. Pat. Nos. 5,265,614 and 5,078,149 as well as JP Patent Nos. 59-49750 and 59-82838 describe the use of such gels based on poly(vinyl alcohol). However, since all these fluids and gels are volatile, they tend to evaporate even at room temperature and need to be kept in a closed environment (e.g., container, vacuum). Although these fluids and gels may possess load-bearing elastic properties for a short period of time, they are not stable upon long term exposure to the environment. At elevated temperature such as 40° C. and higher, the evaporation rate consistently increases, thereby further shortening the usefulness of the product. Furthermore, water freezes at 0° C., making this type of gel or fluid unsuitable for subzero temperatures. Consequently, hydrogels are only useful as ultrasound transmission media for a limited application, i.e., where the application does not require the gel to last beyond a short period of time.

When the application requires a gel that can be used for days or longer, stable soft elastomeric gel types are required. The elastomeric gels contain an elastomeric network with a high percentage of diluents which are generally nonvolatile at ambient temperatures. They possess elastic and load bearing properties at ambient conditions for a prolonged period of exposure (e.g., several month to a few years). They are stable and maintain elastic properties over a wide temperature range, i.e., from subzero temperatures to 70° C. The art distinguishes two categories of stable soft elastomeric gels: thermoset gels and thermoplastic gels. Thermoset gels are made of a chemically bonded three-dimensional elastomeric network which entraps a large amount of low volatility liquids or diluents. The elastomeric network is permanent and cannot be reversed to a liquid state through heating. A certain amount of diluent is necessary in order to ensure good conformability of the gel to the skin and low attenuation for ultrasound transmission while still maintaining the load bearing properties. In the absence of the required amount of diluent, the gel would resemble common rubber or elastomer which generally have a hardness of greater than 15 Shore A (ASTM D2240). For example, U.S. Pat. No. 4,901,729 describes the use of peroxide crosslinked polybutadiene, sulfur crosslinked polybutadiene, and silicone rubber as ultrasound propagation media. Examples of thermoset gels are silicone gels and polyurethane gels.

The elastomeric network of a silicone gel is formed by silicone rubber which is typically cured by reacting a hydride silicone rubber with a vinyl silicone rubber in the presence of a platinum catalyst. Both silicone rubbers are highly diluted with a non-reactive, low volatility silicone fluid prior to the reaction. The reaction can be carried out at 110° C.–120° C. for 30 minutes, or at room temperature for 48 hours. The silicone gels can also be made by using a silane terminated silicone elastomer which can be cured by exposure to ambient moisture. At the end of the reaction, the final composition contains about 5–45% silicone rubbers and 95–55% silicone fluid. A typical silicone gel composition is exemplified in U.S. Pat. No. 3,020,260, which is incorporated by reference herein. Some commercially available silicone gels include Dow Corning DC 3-4150, DC 3-4154, and Q3-6575; Sylgard 527; Gelest Gel D200 and D300; and P065 2-part and F065 one-part. Other silicone gel suppliers include General Electric Silicones of USA, Wacker Chemie of Germany, Shin-Etsu of Japan, and others. Silicone gels have been used for filled prosthesis devices as described in U.S. Pat. No. 4,455,691 and as sealants as described in U.S. Pat. Nos. 5,290,826 and 5,245,980. U.S. Pat. Nos. 5,747,694 and 5,900,554 and their foreign equivalent, JP Patent No. 9043076, describe the use of a silicone gel in sealing a pressure sensor. U.S. Pat. No. 5,457,352 describes the use of a silicone elastomer applied during the gel phase of the adaptation layer in an ultrasonic converter, wherein the composition contains a large proportion of high density metal oxide for damping or blocking the ultrasonic wave.

The elastomeric network of a polyurethane gel is formed by reacting an isocyanate terminated rubber or oligomers (e.g., polybutadiene, polyisoprene, polytetrahydrofuran, or dimmer acid) with a hydroxyl terminated rubber or oligomers (e.g., polybutadiene, polyisoprene, ethylene-butylene rubber, ethylene-propylene rubber, castor oil, or the like). Each rubber or oligomer is highly diluted with a nonvolatile and compatible diluent prior to the reaction. The diluents include mineral oils, vegetable oils, dibutyl phthalate, dioctyl phthalate, polybutenes, paraffinic oils, naphthenic oils, and the like. The final composition contains about 5–45% reactive rubbers and 95–55% total diluents. A typical polyurethane gel is described in U.S. Pat. Nos. 5,083,940; 4,982,054 and 4,962,286, which disclose the use of polyurethane gels as sealant in electrical or telecommunication junction boxes. GB Patent No. 2,036,504 teaches the use of polyurethane rubber with International Rubber Hardness Degree (IRHD) of 15–50.

A thermoplastic gel is generally made of a thermoplastic elastomer with a large proportion of interdispersed diluent. Thermoplastic elastomers include block copolymers such as styrene-butadiene-styrene, styrene-isoprene-styrene, styrene/ethylene-cobutylenes/styrene (e.g., Kraton polymers by Kraton Inc). Other commercially available block copolymers include Septon polymers, which are styrene/ethylene-co-propylene/styrene (e.g., by Kuraray of Japan). In both, Kraton and Septon polymers, the styrene end blocks form glassy domains at room temperature. The glassy domains act as physical crosslinks that provide the elastomeric properties of the polymer. During heating above the glassy transition temperature of styrene, i.e., about 100° C., the glassy domains melt and the polymers reverse to a liquid state. During cooling, the glassy domains re-form again. Hence, the process is reversible, unlike that in the thermoset gels. Other block copolymers, such as ethylene(ethylene-co-butylene)-ethylene copolymers which contains crystalline polyethylene end blocks, can also be used to prepare thermoplastic gels. The crystalline end blocks form crystallites which act as physical crosslinks to give elastomeric properties, rather than glassy domains as in the styrene based block copolymers. During heating, the crystallites melt and revert to the liquid state. During cooling, the crystallites re-form again. Similarly, the process is reversible.

In order to form a gel with thermoplastic elastomers, a large amount of low volatility diluent (e.g., typically 65–95% diluent) is used together with 5–35% block copolymers. The block copolymer may be a styrene/ethylene-co-butylene/styrene block copolymer with a total molecular weight of 30,000 to 300,000. The molecular weight of each styrene block may range from 4,000 to 35,000, and the molecular weight of the ethylene-cobutylene may range from 22,000 to 230,000. The weight percentage of the glassy polystyrene blocks is typically 20–40%, wherein the remaining 60–80% includes the center ethylene-co-butylene elastomer block. The suitable diluents include mineral oil, paraffinic oil, naphthenic oil, polybutenes, and the like, so long as they are compatible with the rubbery center portion of the block copolymers. Examples of gel composition based on block copolymers are described in U.S. Pat. Nos. 4,369,284 and 4,618,213, incorporated by reference herein. U.S. Pat. No. 4,618,213 describes the use of gels as toys or as acoustic isolators for noise reduction. U.S. Pat. Nos. 5,994,446; 5,925,707; and 5,710,206 describe thermoplastic gels for sealing applications. U.S. Pat. Nos. 6,406,499; 5,985,383; 5,925,707; 5,830,237; and 5,766,704, describe the use of thermoplastic gels for cushioning or shoe sole applications. U.S. Pat. Nos. 6,066,329 and 5,879,694 teach the use of thermoplastic gels for making transparent candles. U.S. Pat. No. 5,830,136 teaches the use of thermoplastic elastomer gel in optical sensors. All patents and publications are incorporated by reference herein.

Both thermoplastic and thermoset gels may be used in the instant invention. The gels used herein are generally defined by the following properties:

(i) Hardness: 5<Needle Penetration<300($\frac{1}{10}$ mm) according to ASTM D15, preferably 25<Needle Penetration<150, and most preferably 30<Needle Penetration<50.

(ii) Strength: 5<Tensile Strength<500psi (pounds per square inch) according to ASTM D412, preferably from 10 to 300 psi, and most preferably from 50 to 200 psi.

(iii) Elongation: 50% <Elongation<800% according to ASTM D412, preferably from 200% to 700%, and most preferably from 300% to 500%.

(iv) Stability: The gels are stable after a stress and temperature cycling (with no oil exuding out).

The gels have good adhesion to the plastic housing of the ultrasonic transducer. The plastic housing may include acrylonitrile-butadiene-styrene (ABS), polycarbonate, nylon, and the like. Preferably, the gels are bonded to the plastic housing to form an integral unit. However, the instant invention also encompasses alternative ways to attach gels to the ultrasonic transducer.

In a preferred embodiment of the invention, a thermoplastic gel is over-molded, i.e., directly molded onto the plastic housing of a transducer (including a piezoelectric acoustic actuator and sensor), wherein specific molding techniques are employed. Such techniques are well known in the plastic industry. For example, the plastic encased ultrasonic transducer may be inserted into a mold, wherein a thermoplastic gel is heated to the molten state and injected into the mold by using an injection molding machine. The injection time and temperature of the gel are monitored to prevent damage to the transducer itself. In its molten state, the gel readily flows and eventually adheres to the plastic housing of the ultrasonic transducer (i.e., without using an additional adhesive at the interface between the plastic and the gel). However, in order to ensure a durable bond, it is preferable to apply a thin layer of primer or adhesive onto the surface of the plastic housing before the gel is molded onto it. One such suitable adhesive is a thermoplastic gel which has a lower oil content than the gel to be molded via injection. Several such lower oil containing thermoplastic gels are commercially available, such as Versaflex OM 6000 supplied by GLS Corporation, and Monprene supplied by Telmor Apex Corporation. The extra layer of primer or adhesive functions as a tie-layer between the plastic housing of the transducer and the acoustic transmission gel. The plastic housing can be ABS, polycarbonate or nylon. The surface of the plastic housing is usually cleaned prior to applying the thin layer of primer or adhesive (e.g., with a solvent to remove mold release agents, greases, oils, and dirt). Having a lower oil content, the tie-layer has a higher concentration of polymer on the surface, thus, it can form a strong bond with the plastic surface. Since the tie-layer also contains similar chemical constituents as the acoustic transmission gel, it has good compatibility with the gel at the interface. Optionally, the tie-layer may contain additional ingredients that further improve adhesion to the plastic housing, such as adhesion promoters, compatibilizers, coupling agents, and the like.

In another preferred embodiment of the invention, the tie-layer is over-molded by injection molding. A two-stage insert molding process is preferred, wherein the tie-layer is molded first and the acoustic transmission gel is molded second. This process is particularly preferred for large scale manufacturing, wherein high quantities of product are processed. In an alternative embodiment, the adhesive is pre-dissolved in a suitable solvent to reduce its viscosity so it can be applied as a primer onto the plastic housing. In this technique, the solvent is allowed to evaporate before the over-molding with the acoustic thermoplastic transmission gel takes place. This is particularly useful if the production volume is lower. In yet another alternative embodiment, it is possible to cast the thermoplastic gel onto the tie-layer coated plastic housing of the transducer surface, instead of injection molding. In this technique, the thermoplastic gel is heated to above 150° C., preferably above 160° C., and most preferably above 170° C., and then poured onto the plastic housing of the transducer (which was inserted into a mold). At those temperatures the thermoplastic gel is fluid and can be poured with relative ease. The heating temperature is usually kept below 180° C. to prevent excessive fuming. The flash point of the mineral oil which is used as the diluent in the thermoplastic gel is about 220° C.

Commercially available adhesives may also be used in the instant invention (e.g., adhesives such as EC6000 manufactured by ECLECTIC PRODUCTS, INC., Carson, Calif. 90745). Commercially available adhesives can be employed to bond the acoustic transmission gel onto the plastic housing (e.g., EC6000 adhesive can be brushed onto the surface of plastic housing as thin layer prior to the over-molding of the acoustic transmission thermoplastic gel).

In another embodiment of the instant invention, a thermoplastic gel is directly molded onto the transducer, i.e., the piezoelectric acoustic actuator and sensor rather than onto a plastic housing which contains the transducer. The injection or casting temperature of the thermoplastic gel is carefully monitored to prevent damage to the piezoelectric actuator and sensor by the high temperature. If an adhesive or primer is used, it is applied directly onto the surface of the piezo-electric units prior to overmolding.

In another preferred embodiment of the invention, a thermoset gel, such as silicone or polyurethane, is cast onto the ultrasonic transducer. The gel may be cast directly onto the transducer device itself or onto the plastic housing. Thermoset gels are also available through commercial suppliers and are generally provided in a two-part liquid form (i.e., the gel is then mixed in a preset ratio according to the manufacturer's instructions). The thermoset gel mixture is cast around the transducer which is previously put inside a mold prior to casting.

The casting is left in the mold and heated to a desired temperature to complete curing of the gel. Silicone gels can be cured at an ambient temperature of about 23 C. for 48 hours, or at 120° C. for 1 hour. For polyurethane gels, the initial curing temperature is 1 hour at ambient temperature of about 23 C., followed by post curing at 100° C. for 16 hours. When using thermoset gels in the instant invention, it is also possible to use an adhesive or a primer to ensure good bonding at the interface. For silicone gels, a RTV silicone adhesive or primer can be employed. For polyurethane gels, a polyurethane based adhesive is preferred. In an alternative embodiment, thermoset gels are applied to the transducer by liquid injection molding. The two gel parts are stored in separate tanks, after which they are pumped into an inline static mixer according to the desired preset ratio. The mixture is then injected into the mold to encapsulate the transducer.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An ultrasonic monitor for measuring pulse rate values in a living subject, comprising:
   a) at least one source of ultrasonic energy;
   b) a gel pad comprised of a polymer and from about 50 to about 95% by weight of an ultrasound conductive diluent, wherein said polymer is characterized by having
      i) needle penetration from about 5 to about 300 ($\frac{1}{10}$ mm) according to ASTM D15;
      ii) tensile strength from about 5 to about 500 psi according to ASTM D412; and
      iii) elongation from about 50% to about 800% according to ASTM D412; wherein said gel pad is positioned directly between the energy source and the living subject;
   c) an ultrasonic energy detector; and
   d) associated hardware and software for detecting, calculating and displaying a readout of the measured rate values.

2. The ultrasonic monitor of claim 1 wherein said polymer is characterized by having
   i) needle penetration from about 25 to about 150;
   ii) tensile strength from about 10 to about 300 psi; and
   iii) elongation from about 200% to about 700%.

3. The ultrasonic monitor of claim 1 wherein said polymer is characterized by having:
   i) needle penetration from about 30 to about 50;
   ii) tensile strength from about 50 to about 200 psi; and
   iii) elongation from about 300% to about 500%.

4. The ultrasonic monitor of claim 1 wherein said monitor is in the form of a wristwatch with attached wristband.

5. The ultrasonic monitor of claim 1 wherein said source of ultrasonic energy comprises a first and a second piezoelectric crystal, wherein the crystals are positioned at an angle to each other, said angle determined based on the distance of said energy source to the pulse living subject.

6. The ultrasonic monitor of claim 5 wherein said first piezoelectric crystal is energized by an original ultrasound frequency signal, wherein the original ultrasound frequency signal is reflected off the living subject and received by the second piezoelectric crystal, and wherein said received ultrasound frequency signal is higher or lower than said original ultrasound frequency signal depending on direction and speed of fluid flow.

7. The ultrasonic monitor of claim 1 wherein said polymer is selected from the group consisting of acrylonitrile-butadiene-styrene, polyurethane, and silicone.

8. The ultrasonic monitor of claim 1 wherein said ultrasound conducting diluent is selected from the group consisting of dibutyl phthalate, dioctyl phthalate, mineral oils, naphthenic oils, paraffinic oils, polybutenes, silicone fluids and vegetable oils.

9. The ultrasonic monitor of claim 1 wherein the energy source and detector are located within the same module and communicate by wireless transmission with the processing and display hardware.

10. The ultrasonic monitor of claim 9 in the form of a wristwatch.

11. The ultrasonic monitor of claim 1 wherein the energy source and detector are located within the same module and are hardwired to the processing and display hardware.

12. The ultrasonic monitor of claim 11 in the form of a wristwatch.

13. An ultrasonic monitor of claim 1 in which the module is integrated into or held in place by a headband.

14. A method for detecting pulse rates in living subjects, which method comprises providing a monitor of claim 1 and contacting said monitor with the subject at the point where the pulse is to be measured.

15. A method of claim 14 in which the living subject is a human.

16. A method of claim 14 in which the monitor is positioned on the radial or ulnar artery.

17. A method of claim 14 wherein said pulse rates are selected from the group consisting of heart rate values, blood flow rate values, fetal heart rate values, and fetal blood flow rate values.

* * * * *

UNITED STATES PATENT AND TRADEMARK OFFICE
CERTIFICATE OF CORRECTION

PATENT NO. : 6,843,771 B2
DATED : January 18, 2005
INVENTOR(S) : Lo

It is certified that error appears in the above-identified patent and that said Letters Patent is hereby corrected as shown below:

Column 13,
Line 17, after "of" and before "polyurethane" delete "acrylonitrile-butadiene-styrene," and substitute -- styrene-butadiene-styrene, --

Signed and Sealed this

Twenty-second Day of March, 2005

JON W. DUDAS
*Director of the United States Patent and Trademark Office*